United States Patent [19]

Arnold

[11] Patent Number: 4,649,561
[45] Date of Patent: Mar. 10, 1987

[54] TEST PHANTOM AND METHOD OF USE OF SAME

[75] Inventor: Ben A. Arnold, 35 Red Hawk, Irvine, Calif. 92714

[73] Assignee: Ben Arnold, Irvine, Calif.

[21] Appl. No.: 555,608

[22] Filed: Nov. 28, 1983

[51] Int. Cl.$^4$ .............................................. G01D 18/00
[52] U.S. Cl. ................................. 378/207; 250/252.1; 378/18
[58] Field of Search ....................... 378/207, 156–159, 378/18; 250/252.1

[56] References Cited

U.S. PATENT DOCUMENTS

| | | | |
|---|---|---|---|
| 4,344,183 | 8/1982 | Jacobson | 378/207 |
| 4,460,832 | 7/1984 | Bigham | 378/207 |
| 4,472,829 | 9/1984 | Riederer et al. | 378/207 |

OTHER PUBLICATIONS

Lin, "Penetration Quality Measurement for Standardization of Radiographic Image Quality", Medical Physics, vol. 2, No. 1, pp. 5–8, Jan./Feb. 1975.
Digital Subtraction Phantom Operating Manual, General Electric Company.
Napp Chemicals Inc. brochure of Povidone-Iodine, U.S.P.
Tissue Substitutes in Experimental Radiation Physics, D. R. White, Med. Phys. 5(6), Nov./Dec. 1978.
Proceedings of SPIE-The International Society for Optical Engineering, vol. 273, Mar. 22–24, 1981.
Digital Video Angiography System Evaluation by Ben Arnold et al., Nov./Dec. 1981.
Iodine Sensitivity of Digital Imaging Systems-Riederer, et al., SPIE vol. 314, Digital Radiography (1981).
Performance Characteristics of a Digital Fluorographic System by Riederer, et al., SPIE vol. 273, Application of Optical Instrumentation in Medicine IX (1981).

*Primary Examiner*—Craig E. Church
*Assistant Examiner*—Charles Wieland

[57] ABSTRACT

A test phantom and method of fabrication and use of the same is disclosed which phantom is representative of human tissue containing variable concentrations of iodine to serve as a test device in for assessing the performance of X-ray imaging systems such as digital subtraction angiographic apparatus. The method of fabrication provides the long-term stable incorporation of iodine into a tissue equivalent material which allows standardized testing and evaluation of X-ray imaging systems. The incorporation of additional test details into geometrically fixed positions in the phantom allows accurate and reproduceable measurements of other performance parameters of digital X-ray imaging systems.

13 Claims, 5 Drawing Figures

TEST PHANTOM AND METHOD OF USE OF SAME

BACKGROUND OF THE INVENTION

The present invention relates to a test device for radiography and angiography systems and, more particularly, to a test phantom and method of fabrication and use of the same which incorporates stable iodine and other specific test details into a human tissue equivalent material in terms of attenuation and scatter.

As is known, angiography is the diagnostic study of the human cardiovascular system by the injection of iodine contrast materials into either the veins or arteries of a patient and the acquisition of X-ray images of the same cardiovascular system. Digital radiography and digital subtraction angiography are recent developments providing digital electronic X-ray imaging utilizing an X-ray imaging intensifier and a video system in combination with a computer. In addition to other advantages, such technology permits digital subtraction of images whereas one image of the body is taken prior to iodine contrast media injection and a second image is taken following the injection; with the two images then being compared, i.e. by digital subtraction, in the computer to provide an enhanced image of the blood vessels filled with contrast media while removing the overlying influence of bone and other soft tissue. In addition, the sensitivity of digital subtraction angiography systems is in general higher than with conventional film angiography thereby allowing the imaging of lower iodine concentrations in the patient.

The detection of small iodine concentrations in the cardiovascular system thereby facilitates imaging of the blood vessels, in some cases by injection of contrast media into the venous system, a procedure which reduces the risk to the patient while providing cost and time savings to the radiologist. Thus, digital angiography systems have become commercially successful in recent years and are finding widespread use in medical clinical applications throughout the world.

To insure the sensitivity of such digital subtraction angiography systems, however, a test assessment of the performance and imaging capability of such systems is imperative. Although there have been various prior art methods derived for testing and determining system performance, a preferred measurement method comprises the measurement of the level of iodine detectability under the digital subtraction mode of operation of such systems. Properly implemented, this measurement correspond to the systems ability to detect blood vessels of various diameters filled with various concentrations of iodine contrast media. One prior art system for providing an iodine detectability test is that developed by Riederer et al. (Riederer S. J., Di Bianca FA, Georges JPJ et al. Perfound Characteristics of a Digital Fluorographic System, Application of Optical Instrumentation in Medicine IX, SPIE Vol. 273, pp. 88–95. 1981) who constructed a subtraction test phantom using a liquid plastic manufactured by Clear Cast American Handi-Craft Company which solidifies in the presence of a catalyst. The solidified plastic may then be machined to form various channels or holes of desired diameter. Iodo-benzene, an iodine containing substance, is then desolved within a fluid liquid plastic and poured back into the machined channels within the plastic form thereby resulting in a test phantom.

The major problem associated with such prior art test phantoms has been their inability to maintain iodine in a stable format within the phantom over prolonged periods, resulting in the iodine propagating out of the test phantom. Thus, due to this instability of the iodine within the phantom, the use of such prior art phantoms to access performance of digital angiography systems over the normal course of system operation has been deficient.

In addition to the iodine instability deficiencies, the prior art phantom devices have also typically failed to provide a medium which simulates the properties of human blood vessels containing iodine. A third material used for a container of the iodine has not typically been tissue equivalent. As will be recognized, the use of such tissue equivalent media is imperative to insure proper system function during actual angiographic performance applications.

Further, the prior art test phantoms have typically been deficient in providing other non-iodine bearing test details in geometrically fixed positions within the phantom to permit accurate and reproduceable measurement of other parameters of digital X-ray imaging system performance such as video time jitter, system motion, and other error sources in subtraction imaging.

Thus, there exist a substantial need in the art for an improved test phantom representative of human tissue containing small concentrations of iodine in a long-term stable format which additionally includes other test details in geometrically fixed positions to provide a convenient method to accurately determine performance of digital subtraction angiographic systems.

SUMMARY OF THE PRESENT INVENTION

The present invention specifically addresses and alleviates the above-referenced deficiencies associated in the prior art by providing a test phantom and method of fabrication and use of the same which phantom is formed of a material which simulates the properties of human tissue, contains various iodine details in a stable configuration for prolong periods of time, and includes other test details which permit the accurate and reproduceable measurement of performance parameters of radiography and angiography systems.

More particularly, the present invention provides a test phantom device which contains plural, discrete, stable iodine details which respond similar to blood vessel tissue filled with contrast media (iodine containing) in terms of X-ray interactions. The particular iodine details are each provided with differing concentrations of iodine which may be fabricated in geometric configurations adapted to approximate the configuration of human blood vessels. The phantom devices of the present invention additionally contains a variety of other test details, which provide performance parameters of the digital radiography system in a convenient, accurate, and reproduceable fashion.

The method of fabricating the test phantom of the present invention comprises forming the phantom disks of a modified urethane material, forming various iodine details for encapsulation within the phantom disk from a stable chemical complex material containing elemental iodine bound to a low "Z" molecule which is additionally incorporated into a similar modified urethane material. The particular chemical complex utilized in the present invention is polyvinylpyrrolidone-iodine (PVP-I) which has a vapor pressure approximating zero in solution and is highly stable in the absence of amino acids from proteins of bacteria fungi, etc. By fabrication of the overall phantom disks as well as the particular iodine details within the phantom from the same urethane base material, the present invention essentially eliminates the use of a third material to encapsulate the iodine details thus avoiding the potential errors due to X-ray absorption in such a third material.

More particularly, the method of fabrication of the test phantom of the present invention comprises the use of aliphatic urethane which closely mimics or reproduces the X-ray absorption properties of human tissues. In the formation of the iodine bearing details for the phantom, the PVP-I (polyvinylpyrrolidone-iodine) is subsequently mixed with the urethane which due to the hydroscopic properties of the PVP-I, must be baked, dried, and degassed prior to incorporation into the urethane. Similarly, the urethane is also degassed under vacuum to remove all air bubbles and thereby avoid a change in the physical density of the urethane due to the presence of air. The mixture of urethane and PVP-I is then poured into molds of various shapes and configurations to provide the particular iodine test details for the phantom.

Subsequently, these particular iodine test samples may be inserted into the phantom disk or carrier along with other test details and encapsulated therein to provide an airtight enclosed phantom.

The improved test phantom of the present invention formed by the particular method of the present invention has been found to yield a phantom which permits performance evaluations by standardized techniques to verify equipment performance during installation, permits routine quality control checks to verify system performance, allows experimental and technical studies for clinical technique optimization, and facilitates standardized testing to allow comparisons between systems and clinical procedures.

DESCRIPTION OF THE DRAWINGS

These as well as other features of the present invention will become more apparent upon reference to the drawings, wherein.

DETAILED DESCRIPTION OF THE PREFERRED EMBODIMENT

Figure 2:
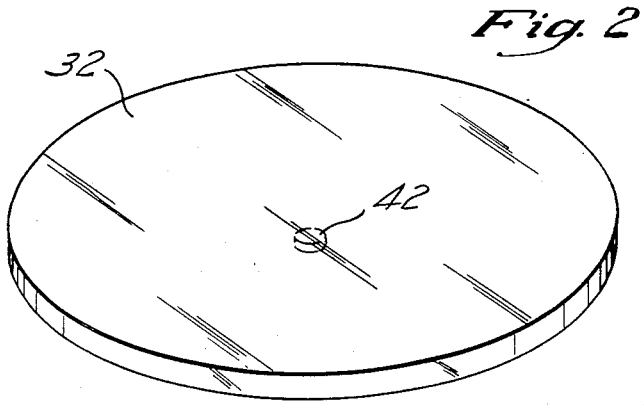
FIG. 2 is a perspective view of a homogeneous test disk containing no test details which forms a portion of the overall test phantom of the present invention.
Figure 1:
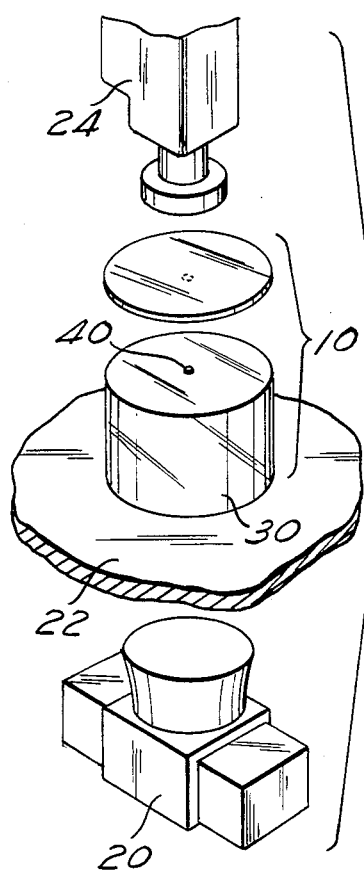
FIG. 1 is a schematic representation of an X-ray imaging system having the improved test phantom of the present invention positioned thereon.

Referring to FIG. 1, there is shown schematically a radiography system such as a digital video radiography system having the test phantom of the present invention disposed thereon. As is well known, the X-ray imaging system is composed generally of a high voltage generator (not shown), X-ray tube 20, a tabletop or platform 22, and an X-ray imaging detector 24 which typically comprises an image intensifier and video camera, screen film or other X-ray sensor. In operation, X-rays emanating from the X-ray tube 20, travel through the X-ray table 22, and test phantom device 10 to impinge upon the X-ray imaging detector 24. The resultant image sensed by the detector 24 may then pass through an amplifier and a computer (not shown) for processing or may be recorded on X-ray film in a developer (not shown). A more detailed discussion of the operation of such digital video X-ray imaging systems is disclosed in an article coauthored by the subject applicant entitled "Digital Video Angiography System Evaluation" published in *Applied Radiology*, December 1981, the disclosure of which is expressly incorporated herein by reference.

Referring more particularly to FIGS. 1 through 4, the test phantom device of the present invention (designated generally by the numeral 10 is preferably composed of four separate elements, i.e. base block 30 (shown only in FIG. 1), a homogeneous test disk 32, an image intensifier test disk 34, and an iodine test disk 36. All of the disks 32, 34, and 36 are adapted to be individually removably mounted to the base block 30 by way of a registry pin 40 extending axially upward from the top surface of the base block 30 which is sized to be tightly received within an axial pocket 42 formed in the lower surface of each of the disk 32, 34, and 36.

In the preferred embodiment, the base block 30 as well as the test disk 32, 34, and 36 are all molded in a generally cylindrical configuration; however, those skilled in the art will recognize that other configurations can be utilized without departing from the spirit of the present invention. The material utilized for the base blocks 30 as well as test disks 32, 34, and 36, comprises a low atomic number material which is approximately tissue equivalent in regards to X-ray absorption properties, which can be easily molded and fabricated into desirable geometries and which in addition, is stable over prolonged time periods. The preferred candidate for such a material has been found to be aliphatic urethane, however, other similar non-urethane components may be utilized.

As is well known, the urethane is composed of a part A and a part B as well as one or more catalyst and stabilizer additives. The part A may typically comprise an isocyanate while part B may comprise an OH substance which when mixed forms an isocyanurate to which various stabilizers may be added. The stabilizers and or catalysts are utilized to prevent discoloration or yellowing of the urethane upon extended radiant exposure as well as to allow solidification of the urethane at room temperatures to prevent bubble formation typically generated when heat curing is utilized. The particular aliphatic urethane utilized in the present invention has the properties of being stable without the loss of material to atmosphere, low viscosity to allow easy fabrication without the production of air bubbles, and a physical density of approximately 1.03 to 1.07 grams per cubic centimeter. The urethane is also similar to human soft tissue in atomic number and contains a water white color which is stable thereby avoiding yellowing. This urethane material may additionally be advantageously dyed to provide a distinctive color which additionally provides the ability to visually determine the locality of the test details in the test disk.

As previously mentioned, the base block 30 and test disks 32, 34, and 36 are preferably molded of this urethane material. To accomplish this molding process, the urethane is formed by combining parts A and B and the stabilizers within a vacuum of approximately 29 inches of mercury to remove any air bubbles generated from the combination of the A and B components. Preferably, a colored dye (such as a purple dye) may then be added to the urethane during formation of the same.

With specific reference to the base block 30, the liquid urethane is poured into a conventional mold (not shown) to form the base block having dimensions of approximately 9 inches in diameter and 4–8 inches or variable thickness. The mold containing the liquid urethane remains under vacuum to remove all air bubbles and to avoid any change in the physical density of the urethane due to the presence of air therein and also to avoid the generation of air pockets within the base block from exotherm which would produce artifacts in the X-ray imaging process. The mold is maintained at room temperature at all times to avoid any further possibility of production of air bubbles and is allowed to cure for approximately 10 to 15 hours thereby additionally reducing any possibility of shrinkage.

The homogeneous test disk 32, image intensifier test disk 34, and iodine test disk 36 are formed in an analgous process with the same liquid urethane material. However, the test disks 32, 34, and 36 are sized to have a finished height of approximately ¾ of an inch. With specific reference to the homogeneous test disk 32, it should be noted that no other test details (as defined in more detail below) are provided therein while various test details are included in the image intensifier test disk 34 and iodine test disk 36.

Figure 3:
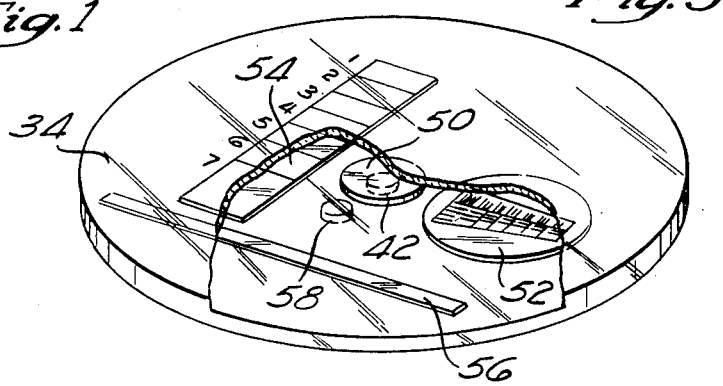
FIG. 3 is a perspective view of an image intensifier test disk which forms a portion of the test phantom of the present invention containing various non-iodine bearing test details.

With specific reference to FIG. 3, the image intensifier test disk 34 includes a contrast ratio test detail 50, a lead bar resolution test pattern detail 52, a dynamic range copper step wedge detail 54, sharp edge metal strip detail 56, and an air contrast detail 58, all of which are encapsulated within the test disk 34. The contrast ratio test detail 50 comprises a circular disk of lead having the diameter of approximately one inch and a thickness of 0.5 millimeters or greater which will provide essentially total absorption of X-rays passing through the test disk 34 during radiography applications. As will be explained in more detail infra, the use of the contrast ratio test disk provides for the measurement of veiling glare, scatter, and video block level.

The lead bar resolution test pattern detail 52 preferably comprises a circular lead member having orthogonal strips varying in spacial frequencies over the expected range of interest, i.e. from 0 to 3.0 lp/mm. The dynamic range copper step wedge detail 54 comprises a plurality of equal thickness copper steps designed to provide a white to black video signal within the respective imaging detector and diagnostic energy range. In the present invention, the steps are formed having a thickness of about 0.12 millimeters and a 1 inch width with the space between the steps being approximately 0.5 inches. The sharp edge metal strip detail 56 is formed from a elongate totally absorbing metal strip with the sharp edge extending across the X-ray field of view. In the preferred embodiment, the detail 56 has a length of approximately 7 inches, a width of approximately 0.25 inches, and a thickness equivalent to 0.1 millimeters of lead or greater. The air contrast circular test detail 58 comprises a void formed within the interior of the disk 34 and is utilized to provide an absolute contrast reference of air versus urethane having dimensions of approximately 1 centimeter in diameter and 2.5 millimeters in height.

In the molding process of the image intensifier test disk 34, a mold similar to that discussed in relation to the homogeneous test disk 32 is utilized, but is initially filled with urethane to only approximately one-half of its overall height. The partially filled mold is then allowed to cure for approximately 12 hours at room or ambient temperature after which time moderate heat is applied to increase the hardness of the urethane. Each of the test details 52 through 58 are then lightly dipped in liquid urethane and placed onto the top surface of the previously cured urethane within the mold. This light dipping of the details 52 through 58 within the urethane helps to avoid any air bubble production during the molding process.

The positioning of the details 52 through 58 within the molding is maintained to precise standards such that the sharp edge detail 56 is located adjacent the distal portion or margin of the disk 34 while the copper step wedge detail 54 is positioned perpendicular to the sharp edge detail 56. In addition, the central axis of the orthogonal lead bar test pattern detail 52 is maintained in a parallel orientation to the axis of the sharp edge detail 56 while the other normal axis of the orthogonal lead bar test pattern detail 52 is positioned perpendicular to the access of the sharp edge detail 56. The lead contrast ratio test detail 50 is preferably positioned in the axial center of the disk 34. After positioning of the details 52 through 58 within the mold in the positions described above, additional liquid urethane is poured into the mold to cover or encapsulate the details 52 and 58 and fix the details 58 in their specific geometric locations and relative orientations. As will be recognized, the liquid urethane is then cured under vacuum and temperature conditions analgous to that previously described.

Figure 4:
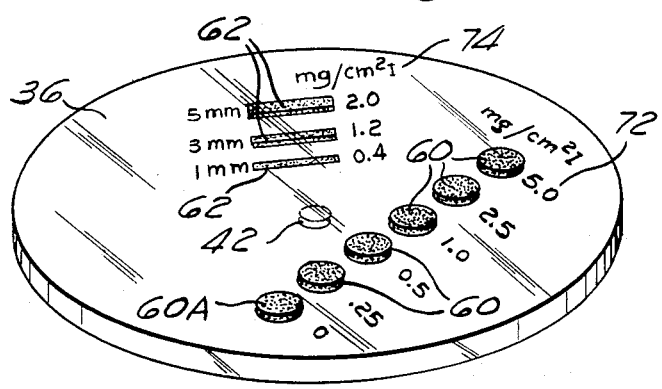
FIG. 4 is a perspective view of the iodine test disk which forms a portion of the test phantom of the present invention which includes iodine containing test details.
Figure 6:
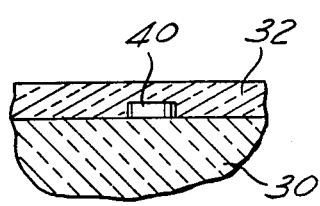
FIG. 6 is a cross-sectional view illustrating the manner in which the test disk of FIGS. 2, 3, and 4 may be positioned upon the base block of the test phantom of the present invention.

Referring to FIG. 4, the detailed construction and method of forming of the iodine test disk 36 may be described. As shown, the iodine test disk 36 includes a plurality of cylindrical iodine test details 60 and one or more elongate iodine test details 62. The cylindrical test details 60 are preferably provided in varying iodine concentrations while the elongate iodine test detail 62 are provided in varying diameter cross-sections simulating arterial and veinous configurations and with varying iodine concentrations. As with the details 52 through 58 of the image intensifier test disk 34, the cylindrical iodine test details 60 and elongate iodine test detail 62 are encapsulated within the interior of the iodine test disk 36. However, to insure that the iodine details 60 and 62 are maintained within the disk 36 in a stabilized form, the details 60 and 62 are fabricated by a specific method and subsequently molded within the disk 36 as inserts.

More particularly, the iodine test details 60 and 62 are formed by first removing any moisture and/or gas from a stable chemical complex or compound containing elemental iodine such as polyvinylpyrrolidone-iodine (PVP-I). PVP-I possesses certain properties such as no detectable vapor pressure in the temperature range of interest, solubility in water, organic solvents and alcohols, no loss of iodine by sublimation or volatilization, and is nonsubliminal at elevated temperatures. Initially, the PVP-I must be elevated in temperature, i.e. to approximately 200 to 250 Fahrenheit under vacuum to remove any moisture and/or gas existing in the PVP-I. Subsequently, the PVP-I is combined with part A of the urethane and mixed in a high sheer mixer to provide even disbursement of the PVP-I within the urethane and then mixed with part B of the urethane. A color dye may then be added to the mixture as described above. The concentration of the PVP-I within the urethane is varied in separate mixing applications with the separate mixtures subsequently being poured into molds suitable to yield the cylindrical and elongate configurations of the iodine details 60 and 62, respectively, preferably having iodine concentrations between 0.01 and 5 mgs/cm.

As best shown in FIG. 4, one of the cylindrical iodine detail 60 is provided with a 0 iodine concentration for manufacturing Quality Control. To form this particular detail (designated by the numeral 60A in FIG. 4), a chemical complex or compound identical to PVP-I is utilized except that the compound does not contain iodine. A suitable candidate for this material is polyvinylpyrrolidone (PVP) which does not contain the iodine atom and has a physical density of 1.03 grams per CC which closely approximates the density of the liquid urethane. The mixing, degassing, and dewatering procedures for PVP are identical to that described in relation to PVP as well as the molding procedure for the insert 60A being identical to that disclosed for the remaining iodine details 60.

Figure 5:
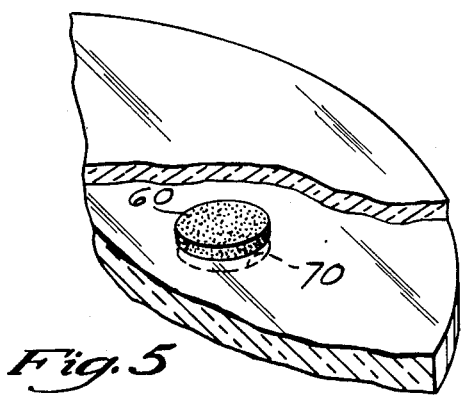
FIG. 5 is a partial perspective view illustrating the manner in which the iodine test details are inserted within the iodine test disk of FIG. 4.

To imbed or encapsulate the particular iodine details 60 and 62 within the disk 36, liquid urethane is poured into a mold in a manner previously described to fill approximately ¾ of the height of the mold. However, in relation to the formation of the iodine test disk 36, the mold includes a plurality of inserts (not shown) sized in a complimentary configuration to the iodine details 60 and 62. As such, upon curing of the liquid urethane poured into the mold, plural pockets 70 (shown as a phantom line in FIG. 5) are yielded in the cured urethane.

After initial curing of the urethane at ambient temperature, the mold and urethane are elevated slightly in temperature to provide a small amount of expansion of the pockets 70 within the urethane. Each of the cylindrical and elongate iodine details 60 and 62 are then dipped or coated in liquid urethane and inserted or pushed firmly into the complimentary-shaped recesses or pockets 70 formed in the cured urethane. Due to the slight expansion of the pockets 70, each of the iodine inserts 60 are firmly seated and bonded in the pocket 70 without any air bubbles existing between the details 60 and 62 and urethane.

After cooling, additional urethane may be poured into the mold to completely encapsulate the details 60 and 62 therein which urethane is then further cured for approximately 12 hours to render a finished iodine disk 36. The cured disk 36 may then be engraved with indicia such as numbering and lettering 72 and 74 to provide quantitative information for the user; and in some instances, the engraved indentations 72 and 74 may then be filled with an opaque material to X-ray such as barium or iodine material so as to provide a reading of the lettering on the final X-ray image. The use of the particular PVP-I material within the urethane has been found to yield an extremely stable iodine detail 60 and 62 which does not propagate or lose its concentration values over prolonged use and further is encapsulated within a urethane medium which approximates the X-ray properties of human soft tissue.

With the structure and method of fabrication of the individual components of the test phantom of the present invention, the overall method of use of the test phantom 10 of the present invention in relation to subtraction radiography applications may be described. Referring to FIG. 1, the base block 30 may be positioned upon the X-ray table 22. Subsequently, the homogeneous test disk 32 may be positioned upon the top surface of the base block 30 with the registration pin 40 of the base block being inserted within the complimentary-shaped registry pocket 42 formed in the lower surface of the disk 32. With the disk 32 positioned upon the base block 30, the X-ray source 20 may be energized causing X-rays to travel upward through the table 22, test block 30, and disk 32 to be received by the X-ray detector 24. As will be recognized, the base block 30 serves as a scattering media having properties closely approximating the properties of human soft tissue while the homogeneous test disk 32 is utilized to provide a similar tissue-like mass having the same size and X-ray absorption as the iodine test disk 36 and image intensifier disk 34 for accuracy and subsequent subtractions. Upon exposure of the test block 30 and homogeneous test disk 32 to the X-rays, a mask image or first image is acquired which serves as a reference for further calibration and testing of the radiographic system. It should additionally be noted that the particular X-ray exposure of the base block 30 upon the table is determined under a specific set of operating conditions, i.e. KVP, MA, exposure time, geometrical conditions, etc., as utilized in the art.

After initial acquisition of the mask image, the homogeneous test disk 32 may be removed from the base block 30 without disturbing the location of the base block 30 upon the table 22 and subsequently substituted with either the image intensifier disk 34 or iodine disk 36. As will be recognized, upon substitution, the registry pin 40 and registry pockets 42 formed on the lower portion of the disk 34 and 36 insure that each of the disks 34 and 36 are properly positioned upon the base block 30. Assuming that the iodine test disk 36 is positioned upon the base block 30, a second X-ray image is acquired under precisely the same set of exposure and operating conditions. The initial mask image and second image may then be digitally subtracted by the computer (not shown) in a conventional manner to provide image enhancement or to obtain more quantitative test results from the images.

The base block 30 and iodine disk 36 may therefore be used to provide a reproduceable test object for measurement of system signal-to-noise ratio and detail signal to noise ratio. This is accomplished by placing an Area of Interest (AOI), containing some 100 pixels, for example, into the center of one of the iodine circular test details 60. The test details 60 are preferably designed to be large enough to provide an area greater than 100 pixels and also are designed to be large enough to produce nonresolution limited test details. After such positioning and exposure, the computer can be used to calculate the standard deviation of noise fluctuations in the image in that particular area of interest after which a similar area of interest may be defined adjacent to but not behind the iodine test details 60 with similar computer calculation being carried out. The results of this test may then be used to further calculate the contrast and detail signal to noise ratio or, alternatively, the image may be used to determine the minimum visually detected iodine detail in both the case of the cylindrical iodine test detail 60 and the elongate iodine test detail 62 which results form a performance criteria iodine detectability.

Similarly, the iodine test disk 36 may be removed from the test block 30 and substituted with the image intensifier test disk 34. A subsequent X-ray image may then be acquired. The contrast ratio test detail 52, alternatively, allows the measurement of the system contrast ratio in cases where the base block 30 and substraction are not utilized which measurement can provide the magnitude of veiling glare either subjectively or quantitatively after analysis in the computer. Such a measurement can also indicate proper setup of the black level of the video chain and its proper matching with the levels of the analog-to-digital converter at the computer input. The circular contrast ratio test detail 42 can also be used to measure scatter-to-primary ratio of scatter radiation generated in the base block 30 which measurement is accomplished by positioning the disk 36 onto the reverse side of the base block such that the X-rays impinge upon the image intensifier disk 34 before passing through the base block 30 and subsequently striking the image detector 24.

In its normal operational position, the disk 34 is preferably positioned upon the base block 30 such that the sharp edge detail 56 will be positioned perpendicular to the horizontal sweep lines of the image detector 24. In addition to other purposes, this positioning allows the lead bar test detail 52 to be disposed such that the two axis of the orthogonal groupings of the detail 52 are positioned perpendicular and horizontal, respectively, to the television scan lines. As such, simultaneously measurement of horizontal and vertical resolution in both the imaging chain and the total imaging system may be obtained. The image of the lead bar test pattern detail 52 can be readily visually analyzed to determine the minimum detectable spatial resolution of the imaging system or alternatively a line of pixel values may be obtained across the image by further computer analysis which values may be used to compute more advanced imaging parameters such as line spread functions and modulation transfer functions of the system.

The dynamic range copper step wedge detail 54 is designed to provide a dynamic range of white to black video signals in the diagnostic energy range of approximately 60 through 120 kvp. In this regard, it provides a dynamic range of absorption in approximately a 50 to 1 ratio. The step wedge detail 54 can be used to verify operation of the log amplifier of the system accomplished by determining the intensity along the copper steps from the data recorded in the computer and thereby verify the linear response after log processing. Alternatively, this step wedge detail 54 can be used to investigate subtraction capabilities at various intensity levels and thereby determine iodine detectability at various intensity levels. Similarly, the detail 54 may be used to measure system noise versus radiation intensity levels by placing an area of interest on each of the copper steps of the detail 54 and performing calculations as discussed above. Further, the detail 54 may be utilized in combination with an oscilloscope by triggering off the signal of the sharp edge detail 56 and allowing delayed sweep from the signal to any copper step of the detail 54.

The sharp edge detail 56 may be used to calibrate scan linearity and thereby identify time jitter of the X-ray detector 24 and other video components of the system. Similarly, the sharp edge detail 56 can be utilized to verify image misregistration in the case of subtraction imaging which is very important in determining image quality in digital subtraction imaging systems. The presence of pixel shifting along the edge of the sharp edge signals indicates time jitter or motion in the imaging system if randon and nonuniform while if the pixel shifting is regular, other malfunctions in the system may be indicated. The sharp edge detail 56 may alternatively be used to determine the edge response function for the purpose of calculating the line spread function and modulation transfer function of the imaging system. The air contrast detail 58 provides an absolute contrast signal which can be used as a reference standard to verify system contrast of urethane versus air or for comparison to the signals obtained using the iodine test disk 36.

Although for purposes of illustration certain materials, configurations, and sizes have been specified, those skilled in the art will recognize that various modifications can be made to the same without departing from the spirit of the present invention; and such modifications are clearly contemplated herein. In addition, those skilled in the art will recognize that additional test details may be fabricated and encapsulated within the urethane carriers of the disks 32 through 36 such as barium contrast material for use in gastro-intestinal examinations, bone or aluminum mimicking bone details, and meshes or wire screens for the detection of distortion or resolution effects over the surface of the imaging detector.

I claim:

1. A comprehensive X-ray apparatus test device comprising:
    a base block sized to be positioned upon a support table of the X-ray apparatus;
    a plate-like member formed to be removably mounted in a generally contiguous orientation upon said base block;
    a plurality of test details disposed within said plate-like member; and
    means for reproducibly aligning said base block with said plate-like member in said generally contiguous orientation, said base block and plate-like member being formed of a urethane material possessing X-ray absorption properties substantially similar to human soft tissue and;
    said test details being formed of a stable iodine bearing material capable of maintaining its concentration value over prolonged use.

2. The device of claim 1 wherein said plurality of test details further comprises a contrast ratio test detail for measuring and comparing the scatter of the X-rays.

3. The device of claim 2 wherein the plurality of test details further comprising a lead member for testing linearity and time jitter of video components; and a plurality of orthogonal strips, said strips disposed in varying spatial frequencies.

4. The device of claim 3 wherein the plurality of test details further comprise a lead bar resolution test pattern detail for testing X-ray scatter, said test pattern detail totally absorbing metal strip having a sharp edge and being formed of an X-ray absorbing material.

5. The device of claim 4 further comprising a dynamic range copper step wedge detail for testing white to black video signals, said dynamic range copper step wedge detail further comprises a plurality of equal thickness copper strips.

6. The device of claim 5 further comprising an air contrast test detail to provide an absolute densitometer reference, said detail further comprising the test disk being formed to create a void.

7. The device of claim 6 wherein said urethane material comprises aliphatic urethane.

8. The device of claim 7 wherein said iodine/urethane mixture comprises a mixture of aliphatic urethane and polyvinylpyrrolidone-iodine.

9. A comprehensive X-ray apparatus test device comprising:

a disc-like member formed to be removably mounted upon a support table of an X-ray apparatus; and an iodine bearing detail disposed within said disc-like member in a stabilized condition;

said iodine-bearing detail being formed of a polyvinylpyrrolidone-iodine material, which maintains its concentration values over prolonged use; and said disc-like member being formed of a substantially human tissue equivalent material with respect to X-ray attenuation and absorption characteristics.

10. The device of claim 9 wherein said iodine bearing detail comprises a plurality of iodine bearing details having differing stable iodine concentrations.

11. The device of claim 10 wherein said plural stable iodine bearing details are formed in differing configurations.

12. The device of claim 11 wherein said substantially human-equivalent material comprises a urethane material.

13. The device of claim 12 wherein said urethane material comprises an aliphatic urethane material.

* * * * *